United States Patent [19]
Hillstead

[11] Patent Number: 5,116,318
[45] Date of Patent: May 26, 1992

[54] DILATATION BALLOON WITHIN AN ELASTIC SLEEVE

[75] Inventor: Richard A. Hillstead, Miramar, Fla.

[73] Assignee: Cordis Corporation, Miami Lakes, Fla.

[21] Appl. No.: 362,251

[22] Filed: Jun. 6, 1989

[51] Int. Cl.$^5$ .............................................. A61M 29/00
[52] U.S. Cl. ........................................... 604/96; 604/8; 606/191; 606/192; 606/194; 606/195; 606/198
[58] Field of Search ............... 606/191, 192, 194, 195, 606/198, 200; 604/8, 96

[56] References Cited

U.S. PATENT DOCUMENTS

| | | |
|---|---|---|
| 3,045,677 | 5/1960 | Wallace . |
| 3,173,418 | 1/1961 | Baran . |
| 3,814,137 | 6/1974 | Martinez ........................... 138/103 |
| 3,889,685 | 6/1975 | Miller, Jr. et al. ............... 606/192 X |
| 4,141,364 | 2/1979 | Schultze ........................... 128/349 |
| 4,195,637 | 4/1980 | Gruntzig et al. ................. 128/348 |
| 4,323,071 | 4/1982 | Simpson et al. .................. 128/343 |
| 4,338,942 | 7/1982 | Fogarty ............................ 128/344 |
| 4,351,341 | 9/1982 | Goldberg et al. . |
| 4,406,656 | 9/1983 | Hattler et al. .................... 604/280 |
| 4,423,725 | 1/1984 | Baran et al. . |
| 4,479,497 | 10/1984 | Fogarty et al. .................. 606/194 |
| 4,553,545 | 11/1985 | Maass et al. ..................... 606/198 |
| 4,580,568 | 4/1986 | Gianturco ........................ 128/345 |
| 4,606,347 | 8/1986 | Fogarty et al. .................. 606/194 |
| 4,636,195 | 1/1987 | Wolinsky . |
| 4,638,805 | 1/1987 | Powell . |
| 4,693,243 | 9/1987 | Buras . |
| 4,710,181 | 12/1987 | Fuqua ............................... 604/96 |
| 4,732,152 | 3/1988 | Wallstén et al. ................ 606/191 X |
| 4,763,653 | 8/1988 | Rockey ............................ 606/194 |
| 4,776,337 | 10/1988 | Palmaz ............................. 128/344 |
| 4,795,458 | 1/1989 | Regan .............................. 623/1 |
| 4,800,882 | 1/1989 | Gianturco ........................ 604/194 |
| 4,811,737 | 3/1989 | Rydell .............................. 128/344 |
| 4,824,436 | 4/1989 | Wolinsky . |
| 4,856,516 | 8/1989 | Hillstead ......................... 128/343 |
| 4,886,062 | 12/1989 | Wiktor ............................. 128/343 |
| 4,906,241 | 3/1990 | Noddin et al. ................... 606/194 |
| 4,906,244 | 3/1990 | Pinchuk et al. .................. 606/194 |
| 4,909,252 | 3/1990 | Goldberger ..................... 604/96 X |
| 4,950,227 | 8/1990 | Savin et al. ...................... 604/8 |
| 4,994,033 | 2/1991 | Shockey et al. : |

FOREIGN PATENT DOCUMENTS 0383429 8/1990 European Pat. Off. .

OTHER PUBLICATIONS

"Expandable Intrahepatic Portacaval Shunt Stents," Palmaz et al. AJR: 145, pp. 821–825, Oct. 1985.
"Expandable Intraluminal Graft: A Preliminary Study," Palmax et al., vol. 156, No. 1, pp. 73–77, Radiology, Jul. 1985.
"The Palmaz Stent: A Possible Technique for Prevention of Postangioplasty Restenosis," Levin, vol. 169, pp. 873–874, Radiology, Sep. 1988.
"Intraluminal Stents in Artherosclerotic Iliac Artery Stenosis: Preliminary Report of a Multicenter Study," Palmaz et al., vol. 168, pp. 727–731, Radiology, Sep. 1988.

*Primary Examiner*—Robert A. Hafer
*Assistant Examiner*—Kerry Owens
*Attorney, Agent, or Firm*—Henry W. Collins; Thomas R. Vigil

[57] ABSTRACT

The stent placement dilation balloon assembly comprises a catheter having a distal end, a distal end portion, and a proximal end, a balloon mounted to, about, and around the distal end portion of the catheter which has at least one opening therein communicating with the interior of the balloon, and, an elastic sleeve positioned about and around the balloon. The sleeve has an at rest diameter which is less than the width of the collapsed balloon if the collapsed balloon was allowed, when deflated, to assume a flat shape. A stent is mounted on the sleeve for placement in a vessel in a human body.

18 Claims, 2 Drawing Sheets

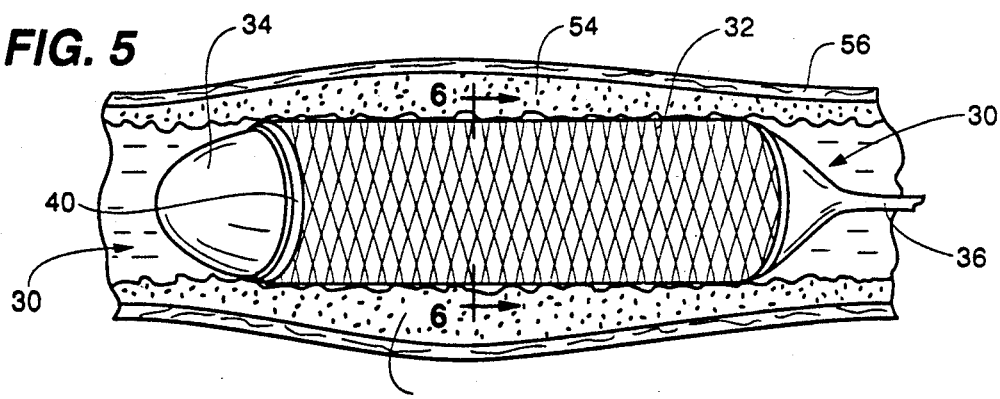
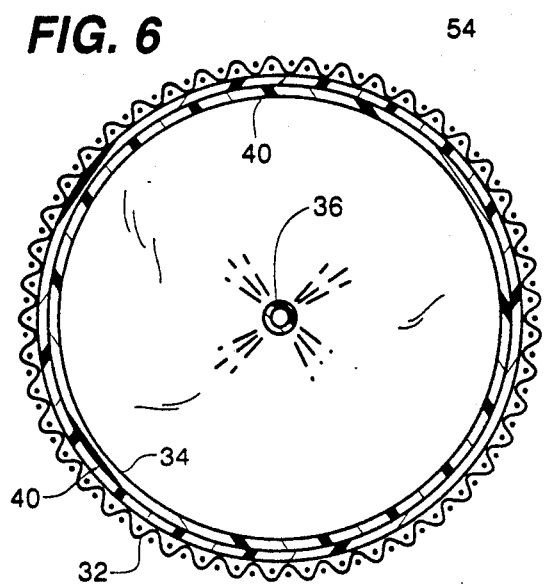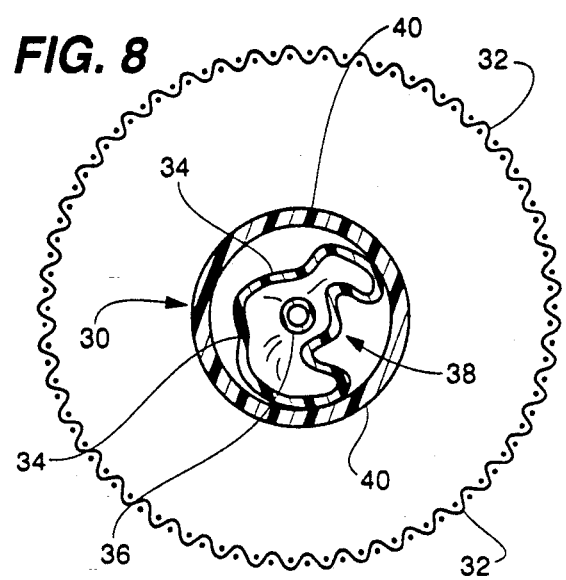
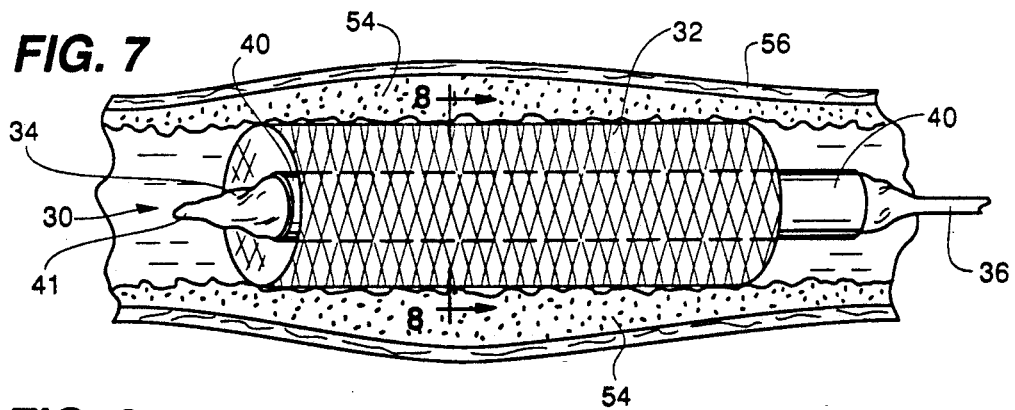
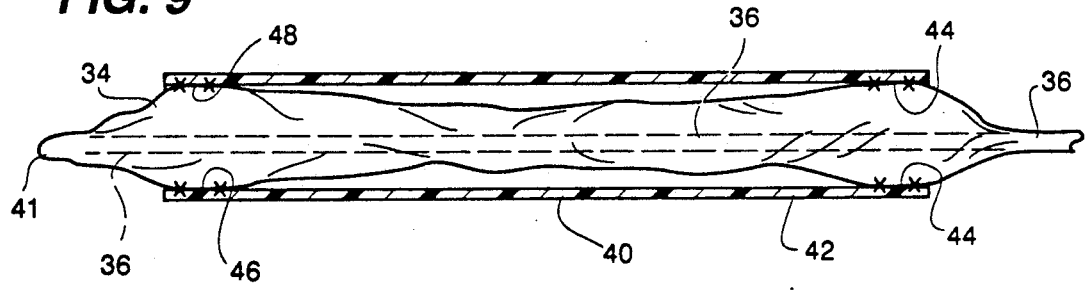

DILATATION BALLOON WITHIN AN ELASTIC SLEEVE

BACKGROUND OF THE INVENTION

1. Field of the Invention

The present invention relates to a dilatation balloon assembly utilized for the implantation of an endoprosthesis device, such as a stent, within a vessel such as a blood vessel in a living body.

2. Description of the Prior Art

Recently endoprosthesis devices, such as stents, have come into more common use in treating stenosis strictures or aneurysms in a blood vessel. Such a device or stent is implanted within a vascular system to reinforce a collapsing, partially occluded or abnormally dilated section of the blood vessel or to effect and reestablish a connection between blocked vessels.

A common procedure for implanting a stent is to first open the region of the vessel with a dilatation balloon catheter. Then, a stent is positioned in the opened area in a position to bridge the opened area, which may be a weakened portion of a blood vessel or an opened area of reconnection between blood vessels.

In the field of angioplasty where a dilatation balloon catheter is placed in a constricted stenotic region and then inflated to expand and open that region, it has been found that the dilating or opening of the restricted stenotic region, while initially relieving the problem of an occluded restricted passageway in the vessel, does not provide a sufficiently long term solution to the problem. In this respect, after a relatively short period of time of a few years the vessel often returns to its original occluded state, i.e., postangioplasty restenosis, as a result of the blood vessel collapsing inwardly or as a result of the rebuilding of plaque in the stenotic region.

What has proved to be more successful is the implantation of a stent after the restricted stenotic region has been dilated. Recent studies indicate that by use of a stent the constriction of the blood vessel in the region of stenotic restriction is maintained open for a much longer period of time than with dilatation alone.

Articles describing the procedures used and the results obtained are set forth below:

"Expandable Intrahepatic Portacaval Shunt Stents," Palmaz et al "AJR: 145", pp. 821–825; October 1985

"Expandable Intraluminal Graft: A Preliminary Study", Palmaz et al, Vol. 156, No. 1, pp. 73–77, "Radiology"; July 1985

"The Palmaz Stent: A Possible Technique for Prevention of Postangioplasty Restenosis", Levin, Volume 169, pp. 873–74, "Radiology" September 1988

"Intraluminal Stents in Atherosclerotic Iliac Artery Stenosis: Preliminary Report of a Multicenter Study", Palmaz et al, Volume 168, pp. 727–731, "Radiology", September 1988

As a result, there is an increasing use of stents and dilatation balloon assemblies for implanting stents. Examples of prior art stents can be found in the following U.S. patents:

| U.S. Pat. No. | Patentee |
| --- | --- |
| 4,140,126 | Chaudhury |
| 4,503,569 | Dotter |
| 4,733,665 | Palmaz |
| 4,776,337 | Palmaz |
| 4,795,458 | Regan |
| 4,880,882 | Gianturco |

Examples of typical prior art dilatation balloon catheter assemblies can be found in the Gruntzig et al. U.S. Pat. No. 4,195,637, the Simpson et al. U.S. Pat. No. 4,323,071 and the Rydell U.S. Pat. No. 4,811,737, the disclosures of which are incorporated herein by reference.

A common problem that has been incurred with the use of dilatation balloon assemblies for implantation of and placement of a stent is the inability of the deflated balloon to disengage from the stent after the stent has been expanded. This phenomena is found most frequently in P.E.T. balloons where the balloon, upon collapsing, tends to flatten out under negative pressure producing a flat or "wing-like" configuration which is wider than the inflated diameter of the balloon ($\pi R$).

In this respect, a 3.0 mm balloon can produce a 4.7 mm wide plane when it is collapsed.

In addition to the disengagement problem found during the stent implanting or placement, the edges of the wings are "blade-like" and sharp enough to cause serious damage to severely diseased (and even healthy) vessels when the deflated, flattened "wing-like" balloon is withdrawn from a blood vessel in a PTCA procedure.

As will be described in greater detail hereinafter, the present invention provides a stent placement balloon assembly including a conventional balloon assembly with an elastic sleeve therearound which results in the balloon expanding within the sleeve which has a stent positioned therearound, the sleeve providing protection to the balloon. Then, when the balloon is collapsed, the elastic sleeve collapses around the collapsed balloon forcing it to a small diameter or small lateral extent eliminating the creation of a "blade-like" or "wing-like" shape in the deflated balloon. This prevents the creation of sharp edges and a width or lateral extent in the deflated balloon greater than the inner diameter of the stent or of the blood vessel through which the stent placement balloon assembly is withdrawn, thereby minimizing if not altogether eliminating the possibility of trauma to the blood vessel when the collapsed/deflated balloon is withdrawn from the stent and the vessel.

SUMMARY OF THE INVENTION

According to the invention there is provided a dilatation balloon assembly comprising: a catheter having a distal end, a distal end portion, and a proximal end; a balloon mounted to, about, and around said distal end portion of said catheter; said catheter having means in said distal end portion thereof for communicating with the interior of said balloon; and, an elastic sleeve positioned about and around said balloon and having an at-rest diameter which is less than the width of the collapsed balloon if the collapsed balloon was allowed, when deflated, to assume a flat shape.

BRIEF DESCRIPTION OF THE DRAWINGS

FIG. 5 is an axial longitudinal sectional view through the blood vessel, similar to the view shown in FIG. 3 and shows a perspective view of the stent and balloon assembly shown in FIG. 3 with the balloon thereof completely expanded or inflated.

FIG. 6 is a diametrical sectional view through the stent and the fully expanded balloon assembly and is taken along line 6—6 of FIG. 5.

FIG. 7 is an axial longitudinal view of the blood vessel shown in FIG. 5 and shows a perspective view of the stent and balloon assembly shown in FIGS. 5 and 6 with the stent expanded but with the balloon of the balloon assembly in a collapsed state.

FIG. 8 is a diametrical sectional view through the expanded stent and collapsed balloon assembly shown in FIG. 7 and is taken along line 8—8 of FIG. 7.

FIG. 9 is an axial longitudinal sectional view through the sleeve of the balloon assembly which sleeve is fixed to the balloon of the assembly and shows a crumpled balloon within the sleeve.

DESCRIPTION OF THE PREFERRED EMBODIMENT

Figure 1:
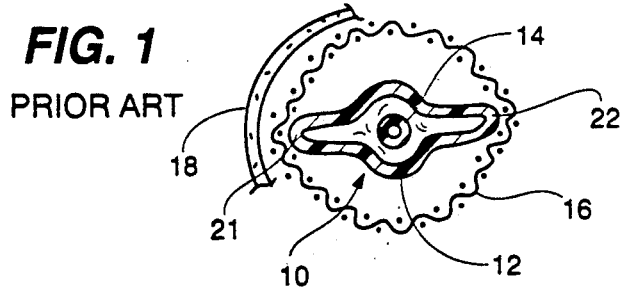
FIG. 1 is a diametrical sectional view through a prior art implanted stent and a prior art collapsed balloon within the stent.

Referring now to the drawings in greater detail, there is illustrated in FIG. 1 a diametrical sectional view through a prior art balloon assembly 10 comprising an outer balloon 12 and an inner catheter 14 to which and about which the balloon 12 is fixed. A stent 16 is received around the balloon 12 and the whole assembly is received within a vessel 18. As is known in the art, the portion of the catheter 14 within the balloon 12 has side ports or openings (not shown) whereby a fluid for inflating the balloon 12 can be inserted through the catheter 14 and the side ports (not shown) into the interior of the balloon 12 which is shown in a collapsed state in FIG. 1.

In its deflated and collapsed state, the balloon 12 tends to assume a flat elongate shape with the width of the flat collapsed balloon 12 being greater than the inner diameter of the stent 16 and often greater than the diameter of the vessel 18 through which the collapsed balloon 12 must now be withdrawn. This "winging" effect results in the creation of "blade-like" edges 21 and 22 of the collapsed balloon 12 which tend to bear against and force outwardly the stent 16 and, as a result of the frictional engagement between the outer edges 21, 22 of the collapsed balloon 12 and the stent, can cause undesired axial displacement of the stent 16 when the collapsed balloon 12 is removed from the stent 16.

Additionally, the collapsed balloon 12 will tend to assume a bowed or curved shape laterally between the edges 21, 22 of the balloon 12. However, the elasticity of the balloon 12 will continue to exert some laterally outward pressure at the outer edges 21, 22 of the balloon 12 against the stent 16 as shown in FIG. 1, and against the vessel 18 through which the balloon 12 is withdrawn.

Although the balloon 12 is made of an elastic material, the edges 21, 22 of the collapsed balloon 12 have a certain degree of sharpness which can result in abrasion to or cutting of the walls of a vessel, such as a blood vessel, when the balloon is withdrawn through a living body. As a result, prior art stent placement balloon assemblies have been known to cause injury to blood vessels.

This susceptibility to causing injury to blood vessels is minimized, if not altogether eliminated, in the stent placement balloon assembly 30 of the present invention shown in FIGS. 2-7.

Figure 2:
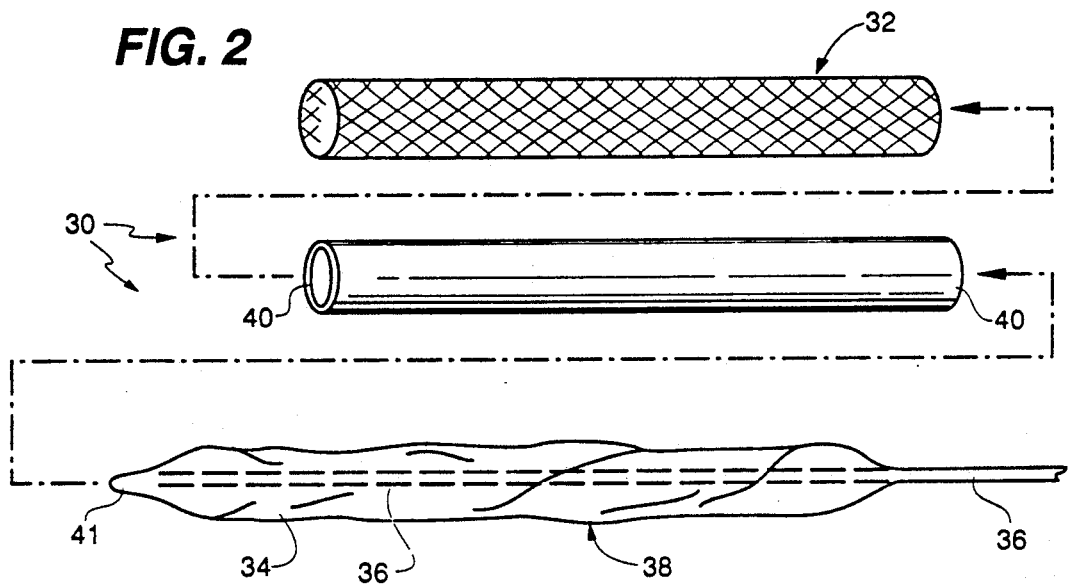
FIG. 2 is an exploded perspective view of a stent and a stent placement balloon assembly of the present invention comprising a dilatation balloon within an elastic sleeve.

In FIG. 2 is illustrated a stent 32 which is adapted to be positioned about the stent placement balloon assembly 30 of the present invention which includes a conventional balloon 34 and catheter 36. The balloon 34, shown partially collapsed in FIG. 2, is fixed to the central catheter 36 to form a conventional balloon assembly 38.

According to the teachings of the present invention, the stent placement balloon assembly 30 of the present invention also includes a cylindrical elastic sleeve 40 which is received over the balloon 34 of the conventional balloon assembly 38.

The conventional dilation balloon assembly 38 comprises a conventional PTA/PTCA balloon catheter 34 and has the elastic sleeve 40 stretched over the entire balloon 34 of the conventional balloon assembly 38.

In the embodiment shown in FIGS. 2-7, the elastic sleeve 40 is stretched over the deflated balloon 34 thus producing a restrictive force which collapses the wall of the balloon 34 tightly over itself and the catheter 36. For this purpose, the elastic sleeve 40 in use will have a diameter smaller than the diameter shown for the sleeve 40 in FIG. 2.

This sleeve 40 can be made of latex having an elongation index of 900%. The sleeve 40 will then be approximately 75% (O.D. to O.D.) smaller than the deflated balloon 34. The sleeve 40 can have an at-rest diameter equal to or less than the diameter of the catheter 36 to provide a very small profile.

In one preferred embodiment, the sleeve 40 is attached to the catheter 36 outer body a short distance proximal of the balloon 34 and extends distally over the balloon 40 to a second point of attachment at or near a distal tip 41 of the catheter 36.

In the embodiment shown in FIG. 9, the sleeve 40 is shown attached to the balloon 34. As shown, a proximal end 42 of the sleeve 40 is fixed at a proximal location 44 and a distal end 46 is fixed at a distal location 48 to the balloon 34.

When the balloon 34 is expanded, the sleeve 40 expands easily, never even approaching its elastic limit. Moreover, the sleeve 40 over the balloon 34 enables the inflation balloon 34 to withstand greater inflation pressures due to the reinforcing effect of the surrounding sleeve 40.

Then, when the balloon 34 is deflated, the sleeve 40 exerts a compression force on the balloon 34 thus reducing its diameter.

At the same time, the thin walled latex sleeve 40 adds very little "bulk" to the catheter, particularly when compared to its compressive elastic force.

As a result of the construction of the balloon assembly 30 of the present invention as described above, the sleeve 40 greatly reduces, if not completely obviates, the "winging" effect frequently observed in the use of conventional PTA/PTCA dilation balloon assemblies (particularly in P.E.T. balloons) by maintaining a constant circumferential pressure force or constriction on the balloon 34 during deflation and subsequent withdrawal of the balloon assembly 34 out of a blood vessel.

If some winging does occur, it will be "contained" within the generally cylindrical sleeve 40 thereby reducing the likelihood of trauma to the vessel.

The reduced "wing" potential greatly facilitates withdrawal of the inflated balloon into a guiding catheter or sheath introducer (not shown).

Also, if the PTA/PCTA balloon should rupture, as does happen from time to time during inflation, there is a reduced potential for vessel damage and virtually no chance of losing a piece of the ruptured balloon in the blood stream particularly when the proximal end 42 and distal end 46 of the sleeve 40 are attached to the balloon 34 or to the catheter 36.

The resilient wall of the sleeve 40 also provides a high degree of protection for the balloon 34 itself, particularly when used to deliver a balloon expandable endoprosthesis device or intravascular stent 32, which has a tendency to puncture a balloon 34 on which it is delivered.

Figure 3:
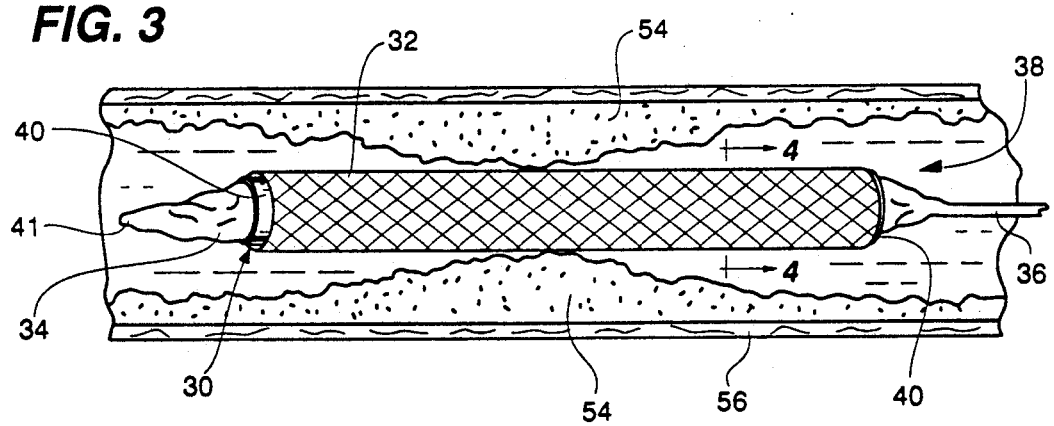
FIG. 3 is an axial longitudinal sectional view through a blood vessel in a living body and shows a perspective view of a stent and a stent placement balloon assembly of the present invention with the stent positioned around a balloon of the assembly and within an area of stenosis in the blood vessel.

FIG. 3 shows the balloon assembly 30 with the balloon 34 within the sleeve 40 and with the collapsible/expandable stent a 32 around the sleeve 40 and shows the whole assembly 30 positioned within an area of stenosis 54 in a blood vessel 56.

Figure 4:
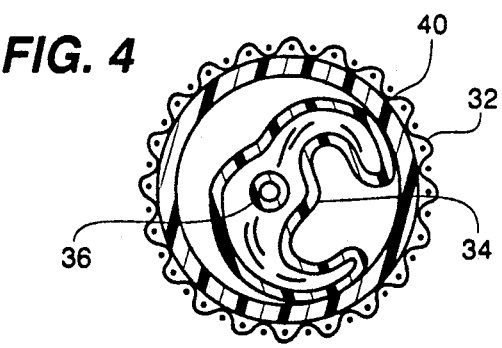
FIG. 4 is a diametrical sectional view through the stent and stent placement balloon assembly shown in FIG. 3 and is taken along line 4—4 of FIG. 3.

FIG. 4 shows the balloon 34 crumpled within the sleeve 40 which is mounting the collapsed stent 32.

FIG. 5 shows a fully inflated balloon 34 and expanded stent 32 pressing the stenotic area 54 radially outwardly and opening the blood vessel 56 as shown.

FIG. 6 shows the cross-section of the fully expanded balloon 34, the expanded sleeve 40 and the expanded stent 32.

FIG. 7 shows the now expanded stent 32 in place and the sleeve 40 and balloon 34 collapsed, ready for withdrawal from the implanted stent 32.

FIG. 8 shows the cross-section of the crumpled collapsed balloon 34 within the collapsed sleeve 40 within the expanded stent 32.

FIG. 9 shows the sleeve 40 fixed at its proximal and distal ends 42 and 46 to the balloon 34. Alternatively, the sleeve 40 is fixed to the catheter 36.

From the foregoing description, it will be apparent that the stent placement balloon assembly 30 having an elastic sleeve 40 therearound of the present invention has a number of advantages, some of which have been described above, and others of which are inherent in the invention. Also, modifications can be made to the assembly 30 of the present invention without departing from the teachings of the invention. Accordingly, the invention is only to be limited as necessitated by the appended claims.

I claim:

1. A dilatation balloon assembly for insertion into a blood vessel comprising: a catheter having a distal end, distal end portion, a proximal end and an overall outer diameter; a dilatation balloon mounted to, about, and around said distal end portion of said catheter and having an interior, an elongate axis, a deflated balloon outer diameter and an at rest collapsed state width; said catheter having means in said distal end portion thereof for communicating with the interior of said balloon; and, an elastic sleeve having a length sufficient to extend the length of said balloon only and not the length of said catheter, being positioned about and around said balloon, being arranged for substantially no axial movement relative to the elongate axis of said balloon so that said sleeve is generally longitudinally coextensive with said balloon at all times, and having an at rest diameter which is less than the width of the collapsed balloon if the collapsed balloon was allowed, when deflated, to assume a flat shape and less than the deflated balloon outer diameter such that said sleeve, when at rest, is in a compressive state compressing said balloon to a smaller diameter.

2. The balloon assembly of claim 1 wherein said elastic sleeve has an elongation index of approximately 900 percent.

3. The balloon assembly of claim 1 wherein said elastic sleeve has an index of elongation and an outer diameter relative to the outer diameter of the deflated balloon which will enable said sleeve to be 75 percent smaller, O.D. to O.D., than the deflated balloon.

4. The balloon assembly of claim 1 wherein said elastic sleeve is fixed to said catheter at its proximal end and at its distal end around and about said balloon.

5. The balloon assembly of claim 1 wherein said sleeve is collapsible around said balloon to a diameter equal to or less than the overall outer diameter of said catheter.

6. A stent placement balloon assembly for insertion into a blood vessel including: a collapsible/expandable stent and a dilatation balloon assembly, said dilatation balloon assembly including: a catheter having a distal end, a distal end portion, a proximal end, and an overall outer diameter; a dilatation balloon mounted to, about and around said distal end portion of said catheter and having an interior, an elongate axis, a deflated balloon outer diameter and an at rest collapsed state width; said catheter having means in said distal end portion thereof for communicating with the interior of said balloon; and, an elastic sleeve having a length sufficient to extend the length of said balloon only and not the length of said catheter, being positioned about and around said balloon, being arranged for substantially no axial movement relative to the elongate axis of said balloon so that said sleeve is generally longitudinally co-extensive with said balloon at all times, and having an at rest diameter which is less than the width of the collapsed balloon if the collapsed balloon was allowed, when deflated, to assume a flat position and less than the deflated balloon outer diameter such that said sleeve, when at rest, is in a compressive state compressing said balloon to a smaller diameter, and said collapsible/expandable stent being received around said elastic sleeve.

7. The assembly of claim 6 wherein said elastic sleeve has an elongation index of approximately 900 percent.

8. The assembly of claim 6 wherein said elastic sleeve has an index of elongation and an outer diameter relative to the outer diameter of the deflated balloon which will enable said sleeves to be 75 percent smaller, O.D. to O.D., than the deflated balloon.

9. The assembly of claim 6 wherein said elastic sleeve is fixed to said catheter at its proximal end and at its distal end around and about balloon.

10. The assembly of claim 6 wherein said sleeve is collapsible around said balloon to a diameter equal to or less than the overall outer diameter of said catheter.

11. In a dilatation balloon catheter for insertion into a blood vessel, a flexible, elongated member, an inflatable dilatation balloon having a deflated balloon diameter, an elongate axis, and being carried on the elongated member to define an inflation chamber within said balloon, and an inflation conduit extending along said member and communicating with the inflation chamber, the improvement comprising, in combination: said inflatable balloon being surrounded by an elastomeric sleeve having a length sufficient to extend the length of said balloon only and not the length of said catheter, being made of an elastic material proportioned to transversely limit the dimensions of said balloon in deflated condition to predetermined maximum width less than the deflated balloon diameter and being arranged for substantially no axial movement relative to the elongate axis of said balloon so that said sleeve is generally longitudinally co-extensive with said balloon at all times.

12. The balloon catheter of claim 11 in which said inflatable balloon is made of a flexible material of less elasticity than the material of said elastomeric sleeve.

13. The balloon catheter of claim 11 in which said elastomeric sleeve is attached adjacent its proximal and distal ends to said balloon catheter.

14. The balloon catheter of claim 13 in which said elastomeric sleeve has a central portion and the central portion of said elastomeric sleeve is free of attachment to said inflatable balloon.

15. The balloon catheter of claim 11 wherein said elastomeric sleeve has an outer surface and has an expansible stent about the outer surface of said elastomeric sleeve.

16. In a dilatation balloon catheter for insertion into a blood vessel comprising a flexible, elongated member, an inflatable dilatation balloon made of elastic material, having a deflated balloon diameter, an elongate axis, and being carried on the elongated member to define an inflation chamber within said balloon and having a lateral deflated dimension, and an inflation conduit extending along said member and communicating with the inflation chamber, the improvement comprising, in combination: said inflatable balloon being surrounded by an elastomeric sleeve having a length sufficient to extend the length of said balloon only and not the length of said catheter, being made of elastic material and proportioned to transversely limit the lateral dimension of said balloon in deflated condition to a predetermined maximum width less than the deflated balloon diameter and being arranged for substantially no axial movement relative to the elongate axis of said balloon so that said sleeve is generally longitudinally co-extensive with said balloon at all times, said inflatable balloon being made of a flexible material of less elasticity than the material of said elastomeric sleeve, and said elastomeric sleeve being attached adjacent its proximal and distal ends to said balloon catheter.

17. The balloon catheter of claim 16 in which said elastomeric sleeve has a central portion and the central portion of said elastomeric sleeve is free of attachment to said inflatable balloon.

18. The balloon catheter of claim 16 wherein said elastomeric sleeve has an outer surface and has an expansible stent about the outer surface of said elastomeric sleeve.

* * * * *